US011867869B2

United States Patent
Alanazi et al.

(10) Patent No.: US 11,867,869 B2
(45) Date of Patent: Jan. 9, 2024

(54) MULTIPLE POROSITY MICROMODEL

(71) Applicant: Saudi Arabian Oil Company, Dhahran (SA)

(72) Inventors: Amer Alanazi, Dammam (SA); Abdulkareem Alsofi, Dhahran (SA); Ammar Alshehri, Dammam (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 521 days.

(21) Appl. No.: 17/174,136

(22) Filed: Feb. 11, 2021

(65) Prior Publication Data
US 2022/0252757 A1 Aug. 11, 2022

(51) Int. Cl.
*G01V 99/00* (2009.01)
*G06F 30/20* (2020.01)
*E21B 25/00* (2006.01)
*G01V 11/00* (2006.01)
*G06T 7/60* (2017.01)

(52) U.S. Cl.
CPC .......... *G01V 99/005* (2013.01); *E21B 25/00* (2013.01); *G01V 11/002* (2013.01); *G06F 30/20* (2020.01); *G06T 7/60* (2013.01); *E21B 2200/20* (2020.05); *G06T 2207/10081* (2013.01)

(58) Field of Classification Search
CPC .... G01V 99/005; G01V 11/002; G06F 30/20; E21B 25/00; E21B 2200/20; G06T 7/60; G06T 2207/10081
See application file for complete search history.

(56) References Cited

U.S. PATENT DOCUMENTS

| 4,882,763 | A  | * | 11/1989 | Buchan ................. G09B 23/08 |
|---|---|---|---|---|
|   |   |   |         | 382/162 |
| 6,226,390 | B1 |   | 5/2001  | Deruyter et al. |
| 6,714,871 | B1 |   | 3/2004  | Xu et al. |
| 8,725,477 | B2 |   | 5/2014  | Zhang et al. |
| 9,507,047 | B1 | * | 11/2016 | Dvorkin ................. G01V 5/101 |
| 9,898,560 | B2 |   | 2/2018  | Hinkley et al. |
| 2009/0259446 | A1 |   | 10/2009 | Zhang et al. |
| 2012/0221306 | A1 |   | 8/2012  | Hurley et al. |
| 2013/0180327 | A1 |   | 7/2013  | Frederick |
| 2014/0350906 | A1 |   | 11/2014 | Killough |
| 2016/0305237 | A1 |   | 10/2016 | Klemin et al. |
| 2016/0318256 | A1 |   | 11/2016 | Alkhatib et al. |
| 2016/0332329 | A1 |   | 11/2016 | Nguyen et al. |

(Continued)

FOREIGN PATENT DOCUMENTS

CN 108 267 466 A 7/2018

OTHER PUBLICATIONS

Spagnuolo AM, Wright S. Analysis of a multiple-porosity model for single-phase flow through naturally fractured porous media. Journal of Applied Mathematics. May 27, 2003;2003:327-64. (Year: 2003).*

(Continued)

*Primary Examiner* — Chuen-Meei Gan
(74) *Attorney, Agent, or Firm* — Osha Bergman Watanabe & Burton LLP

(57) ABSTRACT

A process of constructing a micromodel for a multiple porosity system includes: drilling a well; coring the well for acquiring core plugs from the well; producing thin section images of the core plugs for acquiring a first feature of the core plugs; and transforming the thin section images to binary images.

21 Claims, 6 Drawing Sheets

10A

10B

(56) References Cited

U.S. PATENT DOCUMENTS

2018/0300947 A1* 10/2018 Alkhatib ................. G06T 17/00
2019/0026405 A1    1/2019 Ramsay et al.
2020/0005013 A1*   1/2020 Zhao ................... G06V 20/695

OTHER PUBLICATIONS

Heidari, S. et al., Oil recovery from fractured reservoirs using in situ and preformed particle gels in micromodel structures, Jrnl. Petro. Explor. Prod. Tech., 9:2309-2317 (2019).
Hsu, S-Y. et al., Thermoplastic Micromodel Investigation of Two-Phase Flows in a Fractured Porous Medium, Micromach., 8(38):1-14 (2017).
Saidian, M. et al., An Experimental Study of the Matrix-fracture Interaction During Miscible Displacement in Fractured Porous Media: A Micromodel Study, Energy Sources, Part A, 36(3):259-266 (2014).
International Search Report for PCT/IB2021/053131, 6 pages (dated Oct. 14, 2021).
Tan, M. et al., Digital core construction of fractured carbonate rocks and pore-scale analysis of acoustic properties, Jrnl. Petro. Sci. Engin., 196 (107771): 1-11 (2021).
Written Opinion for PCT/IB2021/053131, 10 pages (dated Oct. 14, 2021).

* cited by examiner

MULTIPLE POROSITY MICROMODEL

FIELD

The subject matter described herein relates to methods to construct a multiple (for example, triple) porosity micromodel that captures heterogeneity of an actual reservoir.

BACKGROUND

In many carbonate reservoirs, formations may not only be naturally fractured, but they may also be heavily vuggy due to cavities, void spaces, or large pores in the formations. Such reservoirs may include major components such as matrix, fractures, and vugs. Fluid transport across (for example, from or into) variable porosity mediums may become very dynamic when such a reservoir is put into production. Recent micromodel designs and fabrication methods have incorporated fractures (for example, fracture channels). However, they do not fully capture heterogeneity of a reservoir (for example, triple porosity reservoir systems). It is essential to design micromodels that mimic an actual reservoir pore system for an accurate determination of critical flow parameters, and development of reliable numerical simulation models.

SUMMARY

The present disclosed embodiments include methods for accurately capturing porosity variability and/or heterogeneous of a reservoir.

The present disclosed embodiments include processes, methods, and workflows to design and/or construct a heterogeneous physical porous medium (for example, a micromodel) that captures attributes of multiple (for example, triple) porosity reservoir systems. The attributes may include types, distributions, wettability, tortuosity, and/or dimensions (for example, diameters, widths, and/or aspect ratios) of pores, cracks, pore throats, fractures, and/or vugs. In some embodiments, the attributes may vary based on distinctive physical properties (for example, porosity and/or permeability) of the reservoir systems, which may determine fluid movement inside the reservoir systems.

In some embodiments, the reservoir systems and/or the micromodel may include at least three features (for example, fractures, vugs, and matrices). In some embodiments, the reservoir systems and/or the micromodel may include fracture corridors and/or fracture channels. In some embodiments, the reservoir systems and/or the micromodel may include variable porosity.

The present disclosed embodiments may include deep fracture characterizations techniques (for example, imaging and/or logging using NMR or seismic data) to determine critical fracture characteristics (for example, aperture and/or fracture orientation). In the present disclosed embodiment, the methods or processes for designing and/or constructing a micromodel may be beyond simply representing a part of a triple porosity system. Rather, the present disclosed embodiments may include micromodels that incorporate three or more porosity characteristics using more sophisticated fracture and/or vug characterization techniques, resulting in more realistic micromodels (for example, a pore network model of a triple-porosity formation system) and more reliable results in fluid hydrodynamics and/or other critical parameters (for example, reservoir and/or fluid parameters). The present disclosed embodiments may help laboratory studies on fluids, flow behavior, and/or interaction between fluids and pore media of a heterogeneous network be as close as possible to an actual reservoir with heterogeneous characteristics.

Understanding flow behavior and/or fluid exchange at a pore scale in a complicated network is of great significance for an accurate prediction of reservoir depletion processes and/or oil or gas trapping mechanisms, which may improve hydrocarbon recoveries.

In one aspect, the present disclosed embodiments are directed to a process of constructing a micromodel for a multiple porosity system including: drilling a well; coring the well to acquire core plugs from the well; producing thin section images of the core plugs for acquiring a first feature of the core plugs; and transforming the thin section images to binary images.

In some embodiments, the process further includes replicating the binary images for expanding a computer network for modeling the well.

In some embodiments, the process further includes characterizing flow features using one or more fracture characterization techniques for acquiring a second feature of the core plugs.

In some embodiments, the process further includes reconciling the features into the binary images for designing a pattern for the micromodel.

In some embodiments, the process further includes fabricating the micromodel based on the pattern using a computer device.

In some embodiments, the process further includes compacting the micromodel.

In some embodiments, the one or more characterization techniques include formation micro-imager (FMI) logging, pressure transient analysis (PTA), and/or CT scan.

In some embodiments, the multiple porosity system is a triple porosity system.

In some embodiments, the flow features include large vugs and macro fractures.

In some embodiments, the flow features come from sources including one or more of well logs, pressure transient tests, whole cores visual descriptions, and images.

In some embodiments, reconciling the features into the binary images further includes connecting replicates by attaching appropriate pore throats of the same features together.

In some embodiments, the process further includes capturing attributes of the multiple porosity system. The attributes may include types, distributions, wettability, tortuosity, and/or dimensions of pores, cracks, pore throats, fractures, and/or vugs.

In some embodiments, the vugs include a dimeter from about 0.1 mm to 50 mm.

In another aspect, the present disclosed embodiments are directed to a method for generating a micromodel including: drilling a well; coring in the well for acquiring core plugs from zones in the well; characterizing main features in the well; screening the core plugs to select the ones that capture the most porosity features; running deep lab imaging techniques on the selected core plugs for capturing details in the selected core plugs; processing images obtained from previous steps; designing a pattern based on processed images; and sending the pattern to a physical surface for fabricating the micromodel.

In some embodiments, characterizing main features in the well includes using logging and/or PTA testing.

In some embodiments, the method includes generating gamma ray and/or sonic data while drilling to describe fractures along a wellbore.

In some embodiments, deep lab imaging techniques include FMI, where the FMI is conducted in the well.

In some embodiments, deep lab imaging techniques include FMI, where the FMI is conducted over cores in a lab.

In some embodiments, deep lab imaging techniques include a CT scan.

In some embodiments, the details include the size and/or the length of fractures and/or vugs.

In some embodiments, images are taken in 2D and/or 3D.

In some embodiments, the method further includes: compacting the micromodel; and injecting fluids into the micromodel.

In some embodiments, the one or more characterization techniques include formation micro-imager (FMI) logging, pressure transient analysis (PTA), and a CT scan.

In some embodiments, the method includes generating gamma ray and sonic data while drilling to describe fractures along a wellbore.

Throughout the description, where processes are described as having, including, or comprising specific components, or where methods are described as having, including, or comprising specific steps, it is contemplated that, additionally, there are processes of the present invention that consist essentially of, or consist of, the recited components, and that there are methods according to the present invention that consist essentially of, or consist of, the recited steps.

It should be understood that the order of steps or order for performing certain actions is immaterial as long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the present claims. The Background section is presented for purposes of clarity and is not meant as a description of prior art with respect to any claim.

BRIEF DESCRIPTION OF THE DRAWING

A full and enabling disclosure of the present disclosed embodiments, including the best mode thereof, directed to one of ordinary skill in the art, is set forth in the specification, which makes reference to the appended figures, in which.

DESCRIPTION OF CERTAIN ASPECTS OF THE INVENTION

Figure 1:
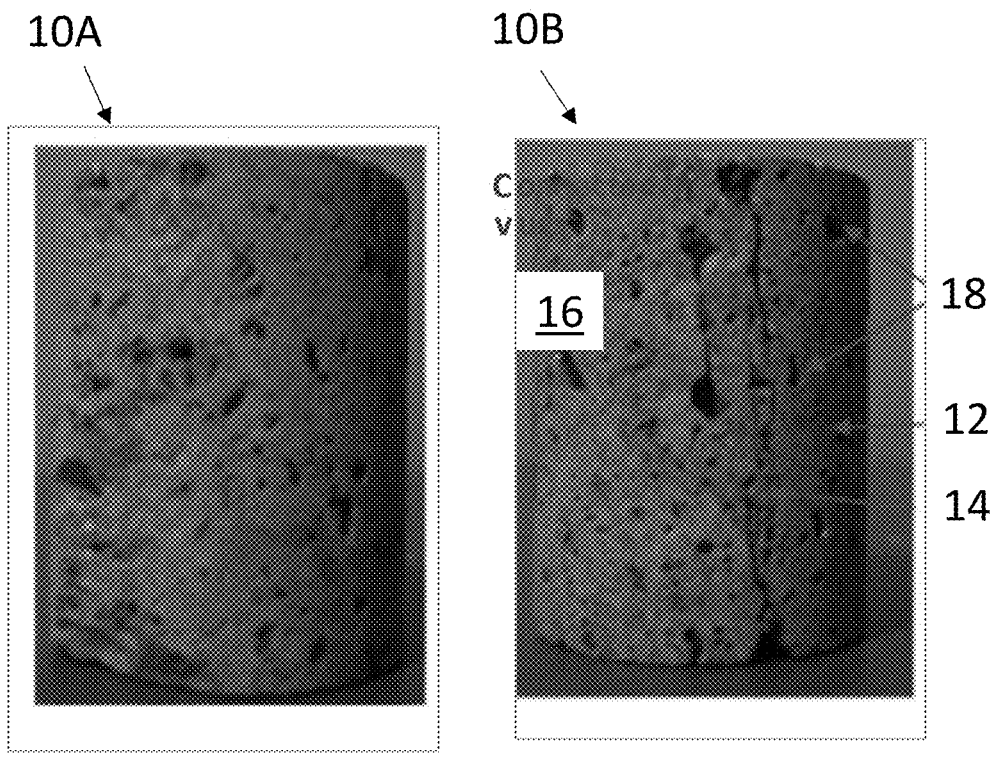
FIG. 1 illustrates exemplary carbonate core plugs or core samples.

Reference will now be made in detail to the present disclosed embodiments, one or more examples of which are illustrated in the accompanying drawings. The detailed description uses numerical and/or letter designations to refer to features in the drawings. Like or similar designations in the drawings and description have been used to refer to like or similar parts of the present embodiments.

Micromodels are widely used to conduct several fundamental studies related to oil and/or gas recovery. Recent micromodel designs have attempted to add fractures (for example, fractures with fixed aperture) to a pore network, but have demonstrated the difficulty of creating a realistic heterogeneous micromodel of an underground formation (for example, rock). Some of these micromodels introduce fracture characteristics to create a dual porosity medium (for example, fractures, and a matrix). However, an actual subsurface rock formation may often be or include triple porosity media that include matrices, fractures, as well as vugs (for example, large void spaces). Vugs may further include non-connected vugs and connected vugs (that is, void spaces that are connected together). Vugs are often not captured in a micromodel for a number of reasons. First, coring operations may fail to maintain a confined pressure over collected cores against the downhole reservoir pressure, resulting in a disintegration of cores that fail to capture some important fracture features (for example, vugs). Second, during plugging of slabbed whole cores, plugs may often be acquired only from a clean core section to avoid further dismantling and/or to avoid external vugs that may be obstacles for various operational and/or analytical procedures (for example, special core analysis (SCAL)). Accordingly, most of the collected core plugs often only carry microfractures in a rock. Such intentional non-sampling practices are what was referred to as avoiding defects using CT or NMR. Besides imaging of whole cores, microscale CT or NMR scans are good tools and are typically used to capture core-scale features, which may capture mostly the matrix of a pore system for the above reasons. The present embodiments include a workflow that attempts to reintroduce the missing large-aperture fractures and vug-networks to build a more realistic fracture micromodel.

Micromodels have been extensively utilized to understand fluid flow behavior and to support the validation of important reservoir parameters such as relative permeability, reservoir capillary/viscous forces, and formation rock wettability. They may physically simulate fluid movement within a structured pore network providing a means for visual observation of the fluid flow behavior. Recent laboratory studies have demonstrated micromodel capabilities for studying fluid flow behavior and conducting various recovery experiments at micro- and macro-pore scales.

Existing micromodels focus on modeling fluid flow across a connected pore network composed of repetitive regions of a pore system of reservoir matrix. The pore system of reservoir matrix may be either manually designed or captured from an image of a core plug thin section. Recent advanced micromodels introduce more heterogeneity into the pore system by adding interconnected fractures channels that intersect with the reservoir matrix. For example, a recent micromodel design includes two fracture channels added into end-edges of a network system to create a linear flow pattern connected with the rest of the network. In another example, a recent micromodel design incorporates a fracture channel with a 45-degree deviation and 500 arbitrary lines with varying lengths and thicknesses to represent non-flowing small channels as dead-ends fractures within a formation.

A micromodel is a fabricated solid structure that represents a reservoir matrix with its different size cavities and pores distribution that can be connected between each other using channels. Previous methods include a construction process of a model that includes etching a pore network into glass. Pore configuration is transposed using a digitized image of pores through light projection of a rock thin section on a glass surface to reproduce pore networks using photolithographic means. Previous methods also include a method of modeling a variable porosity system by having intersecting channels and forming a network of pores of different properties from a thin section. Those networks can be interconnected together to form a unique 3D-geometric model.

Previous studies described the basic principles of designing and construction processes of a pore network. They include physical fabrications and projection of a rock thin section to duplicate its pore configuration. However, they may not incorporate fracture and/or vug characterizations and findings into the design process.

The present disclosed embodiments provides a process to build an advanced micromodel that represents the heterogeneity of a reservoir system, rather than capturing a snapshot of it from only a specific thin section of a core plug, which may cause critical reservoir properties of fluid movements (for example, different coexisting porous media) to be missed.

As described herein, in some embodiments, micro fractures may include a fracture aperture of about 1 to about 999 micro-meters. In some embodiments, macro fractures may include a fracture aperture of more than about 999 micrometers. In some embodiments, a fracture may be a connected pore system that include an orientation and an aperture. In some embodiments, a fracture may appear as a pore space cutting through a rock matrix. In some embodiments, a fracture may cut through a vug and retain its orientation after cutting through the vug. In some embodiments, a vug is a pore void that may be caused by the dissolution of some rock grains in the matrix during part of a transformation process (for example dolomitization and/or biotic dissolution due to bacteria and microbes). In some embodiments, vugs may be large. In some embodiments, vugs may not have an orientation. In some embodiments, vugs may include a width of about 2 mm to about 1 cm. In some embodiments, the differences in orientation and width between a fracture and a vug in a connected fracture-vug system may be determined during a design process. For example, in some embodiments, differences in both the orientations and widths between fractures and vugs are taken into account.

FIG. 1 illustrates exemplary carbonate core plugs or core samples 10A and 10B, which include a triple porosity system. The core plugs 10A and 10B may be collected from one or more formation zones in a naturally fractured carbonate reservoir (for example, an oil or gas reservoir). A core refers to a cylindrical sample of a formation (for example, reservoir rock), taken during or after drilling a well. A core plug (for example, 10A, 10B) may refer to a plug, or sample, taken from a core for analysis. The core plug 10A may include less heterogeneity (that is, the quality of variation in rock properties with location in a reservoir or formation) than the core plug 10B. In some embodiments, the core plug 10B may be taken from a few feet shallower than the core plug 10A. Both core plugs 10A, 10B may include a matrix 12, fractures 14, and vugs, where the vugs may include connected vugs 16, non-connected vugs 18, or combinations thereof.

Referring to FIG. 1, both core plugs 10A, 10B may include heterogeneous formations, in which mineralogy, organic content, natural fractures, and other properties vary from place to place. Both core plugs 10A, 10B may include a multiple (for example, triple) porosity reservoir system, which may include variability of porosity within at least three major features (that is, the matrix 12, the fractures 14, and/or the vugs 16, 18). Fluid movement between complex pore structures in the multiple (for example, triple) porosity reservoir system may become very vigorous once a reservoir depletion starts. At the pore scale, understanding multiphase fluid flow behavior in such a heterogeneous system becomes even more challenging but may be needed to optimize oil and/or gas recovery methods and to develop reliable numerical simulation models.

Figure 2:
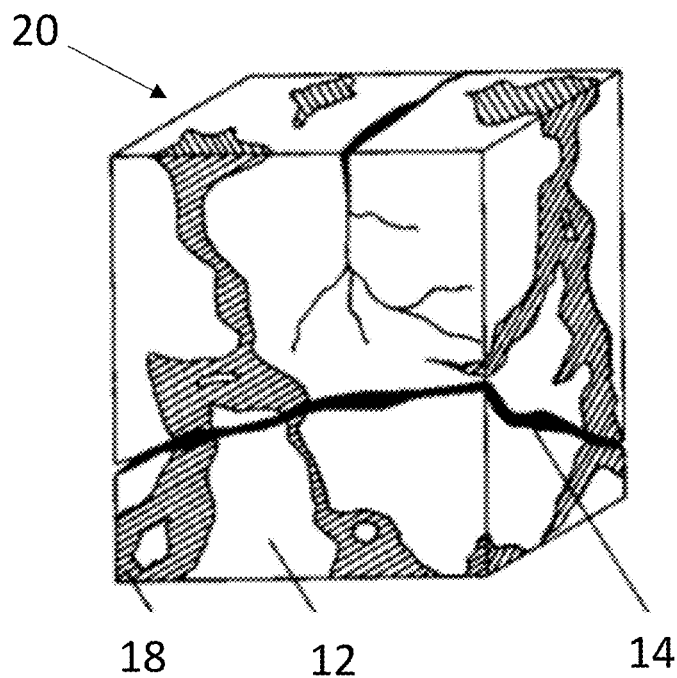
FIG. 2 illustrates a schematic of a triple porosity system, according to aspects of the present embodiments.

FIG. 2 illustrates a schematic of a triple porosity system 20, according to aspects of the present embodiments. The system 10 may comprise the matrix 12, the fractures 14, the connected vugs 16 (not shown), and the non-connected vugs 18. The matrix 12 may refer to finer grained, interstitial particles that lie between larger particles or in which larger particles are embedded within a formation (for example, sandstones or conglomerates). The fractures 14 may refer to a crack or surface of breakage within a formation. The vug (for example, 16 or 18) may refer to a cavity, a void space, or a large pore in a formation (for example, rock) that is commonly lined with mineral precipitates.

Figure 3:
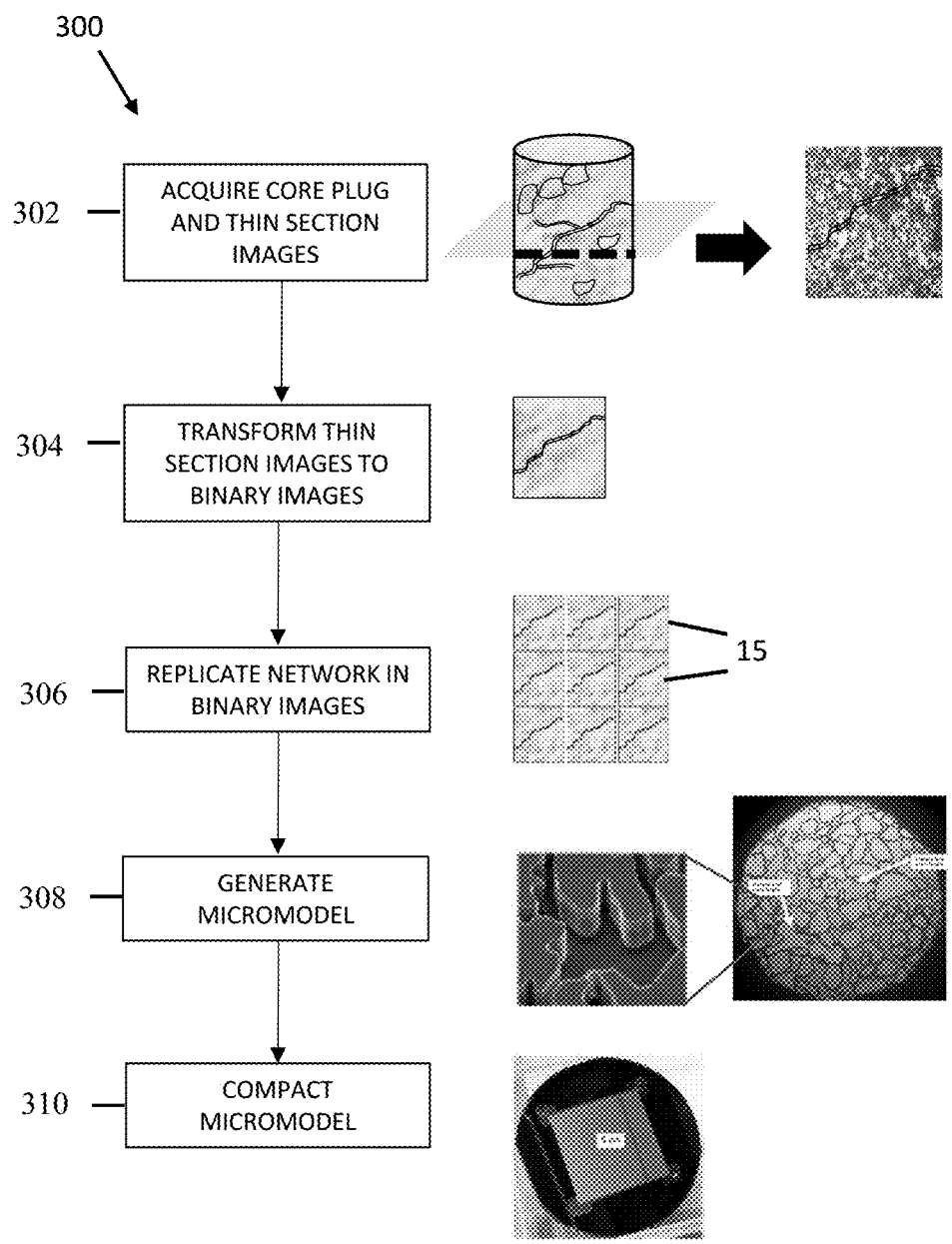
FIG. 3 illustrates an exemplary conventional process for designing and/or constructing a micromodel.

FIG. 3 illustrates an exemplary conventional process 300 for designing and/or constructing a micromodel. At step 302, the process 300 includes acquiring core plug(s) and thin section images. For example, the process 300 may typically use images from thin section CT scans. However, in some embodiments, thin section images may only capture a part of, but not all of the features (for example, matrix pore microfracture systems) of a porosity system. At step 304, the process 300 includes transforming images from step 302 to binary images. At step 306, the process 300 includes expanding pore systems by replicating the network in binary images. For example, in some embodiments, the simplest and widely fabricated scheme for micromodels is constructed by simply residing and attaching replicates 15 next to each other. However, such scheme of design may not be representative of the real formation (for example, rock). At step 308, the process 300 includes generating (for example, etching) a micromodel (for example, layers). At step 310, the process 300 includes compacting the micromodel.

Figure 4:
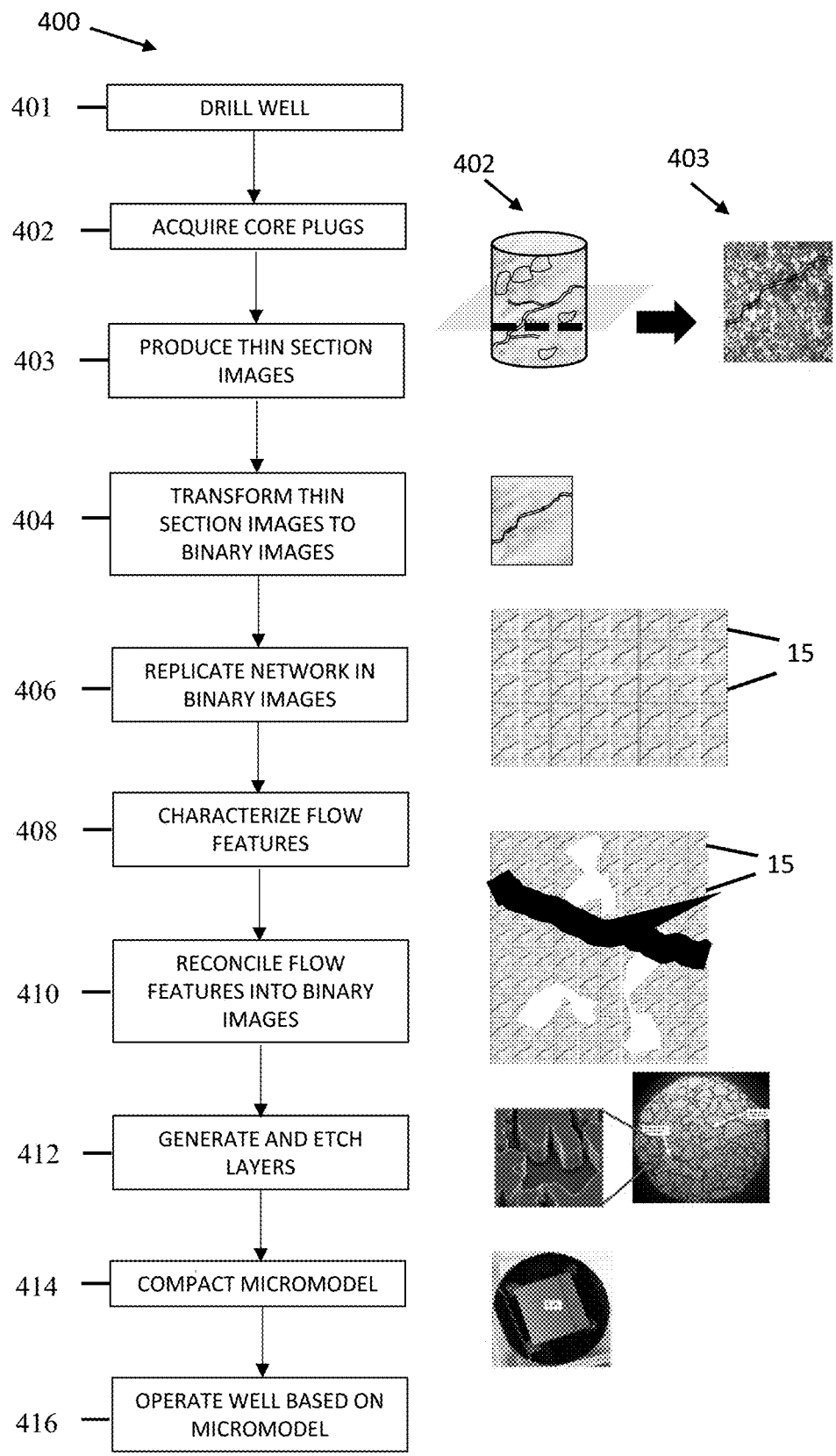
FIG. 4 illustrates a process for fabricating an advanced micromodel, according to aspects of the present embodiments.

FIG. 4 illustrates a process 400 for fabricating an advanced micromodel which represents a more realistic multiple (for example, triple) porosity systems, according to aspects of the present embodiments. In some embodiments, process 300 may miss other features (for example, vugs). Process 400 describes a workflow to design and construct a micromodel that may capture or incorporate at least one more heterogeneity feature (for example, vugs) of a subsurface rock formation than process 300. In some embodiments, process 400 may have applications for constructing a micromodel for a more heterogeneous physical porous medium, resulting in capturing additional attributes of the multiple porosity reservoir systems. The attributes may vary based on distinctive physical properties (for example, porosity and/or permeability), which may influence fluid movement inside the multiple porosity reservoir systems. In some embodiments, process 400 may include deep fracture characterization techniques (for example, nuclear magnetic resonance (NMR) and/or seismic imaging and/or logging) to determine critical fracture elements (for example, fracture aperture and/or direction). More than simply representing a part of the multiple porosity system, process 400 may include or incorporate all triple porosity elements utilizing more sophisticated fracture and/or vug characterization techniques, resulting in more reliable data (for example, data related to fluid hydrodynamics and/or other reservoir and fluid parameters).

Referring to FIG. 4, at step 401, process 400 may include drilling a well. At step 402, process 400 may include acquiring core plug(s) from a multiple (for example, triple) porosity system 10. For example, the core plugs may be acquired from an actual oil or gas reservoir, which includes a multiple (for example, triple) porosity system 10. In some embodiments, standard whole cores may be slabbed, followed by being plugged to obtain smaller core samples (or plugs). In some embodiments, the whole core CT scans may be used to identify sections of interest in standard whole cores that have large diameters for further plugging or to construct a digital core model to understand the attributes of such features (for example, dimensions of fractures). In some embodiments, the core plugs may comprise at least a matrix, one or more vugs, and one or more fractures. In some embodiments, the matrix 12, vugs 16, 18, and/or fractures 14 may be in micro-scale. In some embodiments, the matrix 12, vugs 16, 18, and/or fractures 14 may be in macro-scale. At step 403, process 400 may include producing thin section images, which may further include preparing thin section samples from the core plugs acquired at step 402. In some embodiments, the thin section samples may have a thickness of about 0.01 mm to about 1 mm. In some embodiments, standard thicknesses are sufficient to allow microscopic visualization of the cores and understanding of the rock topology. For example, the thin section samples may be prepared by cleaning, frosting, coating, marking, gluing, and/or cutting the core plugs. In some embodiments, the thin section images may capture at least one of a matrix 12, vugs 16, 18, and/or fractures 14. In some embodiments, the thin section images may capture features of a matrix 12 (such as matrix pores). At step 404, the process 400 may include transforming the thin section images acquired at step 402 to one or more binary images. For example, a color image of the thin section samples may be converted to a black and white image.

Referring still to FIG. 4, at step 406, process 400 may include replicating the network in binary images to produce a higher level expansion of a pore system than step 306 in process 300 described above. In some embodiments, the higher level expansion may be produced through higher-order replication of the network in one or more binary images to allow reconciliation of larger-scale flow features in later steps. In some embodiments, at step 406, the replicates 15 may be attached together based on desired representations in such a way that it would be representative of the overall scheme of a formation pore network.

Referring still to FIG. 4, at step 408, the process 400 may include characterizing high-flow features (for example, large vugs and/or macro-fractures) from different sources (for example, well logs, pressure transient tests, whole core visual descriptions and/or images) by using one or more fracture characterization techniques. In some embodiments, the high-flow features include features resulting from mechanical or chemical deformations which may result in a significant permeability improvement over that of the original rock framework (for example, grains and pores) or matrix. In some embodiments, the fracture characterization techniques include those widely used in the industry. In some embodiments, the fracture characterization techniques may capture features that may not be captured at step 406. In some embodiments, step 408 may include using other measurement tools such as logging techniques (for example, image, resistivity, pulsed neutron, or sonic logs) to determine or characterize the features that may not be captured from a thin section or a core plug 10A, 10B.

Referring still to FIG. 4, at step 410, process 400 may include reconciling characteristic large-scale flow features into the binary image (for example, a large binary image) for designing a pattern for the micromodel. At step 412, process 400 may include generating and/or etching layers (for example, defining boundaries between a first layer and a second layer with respect to at least one characteristic (such as porosity or permeability)). In some embodiments, the etching may include connecting layers without creating a void (for example, a dead volume or a trapped zone). At step 414, process 400 may include compacting a final micromodel. At step 416, process 400 may include operating a well based on results from the final micromodel. For example, work crews may raise or lower operating pressure, temperature, and/or viscosity of drilling fluid within the formation. In another embodiment, work crews may raise or lower the production of a well to match flow characteristics within the formation. In a third embodiment, work crews may take a well offline earlier because the final micromodel predicts lower reservoir flow or production going forward.

Referring still to FIG. 4, step 408 may include using one or more fracture characterization techniques. In some embodiments, the fracture characterization techniques may include Formation Micro-Imager (FMI) logging, which uses the relative resistivity to describe the formation rock pores acquired from the wellbore. In some embodiments, FMI directly measures the micro-resistivity of a formation by using an array of resistivity sensors. In some embodiments, FMI is considered a good tool to describe facies and identify fracture systems in both the wellbore and core scale. Geologists often use core imaging to describe the sedimentology facies of a formation. FMI may be used to obtain information about the fracture directions (upward, downward), tendency, and apertures (length).

Referring still to FIG. 4, at step 408, other techniques may also be used to indicate fractures from wellbores that are not captured by FMI, such as Pressure Transient Analysis (PTA). Pressure Transient Analysis (PTA) may help in characterizing high-flow features based on the permeability and/or the thickness of a zone, as well as the information on zone productivity. PTA may thus be used to confirm productivity of a well and indicate fractures. In the present disclosed embodiments, PTA is preferably used at the early stage of the fracture characterization to confirm which section to use from available cores to get the major fractures in a formation system. The fracture characterization techniques may include CT scans (from a lab), similar to the ones used in the medical industry. As the PTA test is used to get information at the well level, CT scanning is used in the lab to generate a 3D understanding of the pores and matrix of a core. This technique gives in-depth information using imaging technique to measure most of the pore features of a rock.

In some embodiments according to the present embodiments, the vugs may include intercrystalline (dissolved) pores, intergranular (dissolved) pores, dissolved vugs, or combinations thereof. In some embodiments, the dissolved vugs may be characterized as vugs that include a diameter from about 2 mm to about 50 mm, and a surface vug ratio of about 4% to about 81%. In some embodiments, the intergranular (dissolved) pores may be characterized as those that include a diameter from about 0.1 mm to about 1.0 mm, and a surface vug ratio of about 2% to about 15%. In some embodiments, the intercrystalline (dissolved) pores may be characterized as those that include a diameter of about 0.1 mm to about 0.8 mm, and a surface vug ratio (that is, a surface-to-volume ratio of a vug) of about 2% to about 10%. Although there is an overlap in the diameter ranges of intergranular (dissolved) pores and intercrystalline (dissolved) pores, the two types of dissolved pores may develop from different origins. For example, intergranular (dissolved) pores may develop as a result of the influence of acid fluids or atmospheric fresh water leaching, while intercrystalline (dissolved) pores may develop as a result of dolomitization, associated with calcite dissolution processes. In some embodiments, the dissolved vugs may develop as a result of continual dissolution and expansion of dissolved pores, which may be influenced by protolithic facies and atmospheric fresh water dissolution in supergene periods. In some embodiments, the dissolved vugs may develop as a result of local dissolution and expansion along fractures, and may be related to tectonic fractures in uplift periods.

In some embodiments, the process may include characterizing various geometric features and/or types of fractures including reticular fractures, low-angle fractures, oblique fractures, high-angle fractures, and combinations thereof. In some embodiments, the fractures may be formed in the process of tectonic stress or near faults. Structural fractures may be relatively straight, as a result of being dissolved by fresh water or ground water. By contrast, dissolution fractures may include bay shape walls and may be partially filled with dolomite and asphalt. In some embodiments, the reticular fracture may be rarely observed on cores, but may be observed in some cast thin sections. In some embodiments, low-angle fractures may be defined as those that include a density of about 0.01 pics/m, or from about 0.005 pics/m to about 0.05 pics/m. In some embodiments, oblique fractures may be defined as those that include a density of about 0.1 pics/m, or from about 0.05 pics/m to about 0.15 pics/m. In some embodiments, high-angle fractures may be defined as those that include a length of about at least 2 m. In some embodiments, high-angle fractures may be defined as those that include a density of about 0.15 pics/m and higher. In some embodiments, the process may include characterizing various geometric features and/or types of fractures using rose diagrams.

Figure 5:
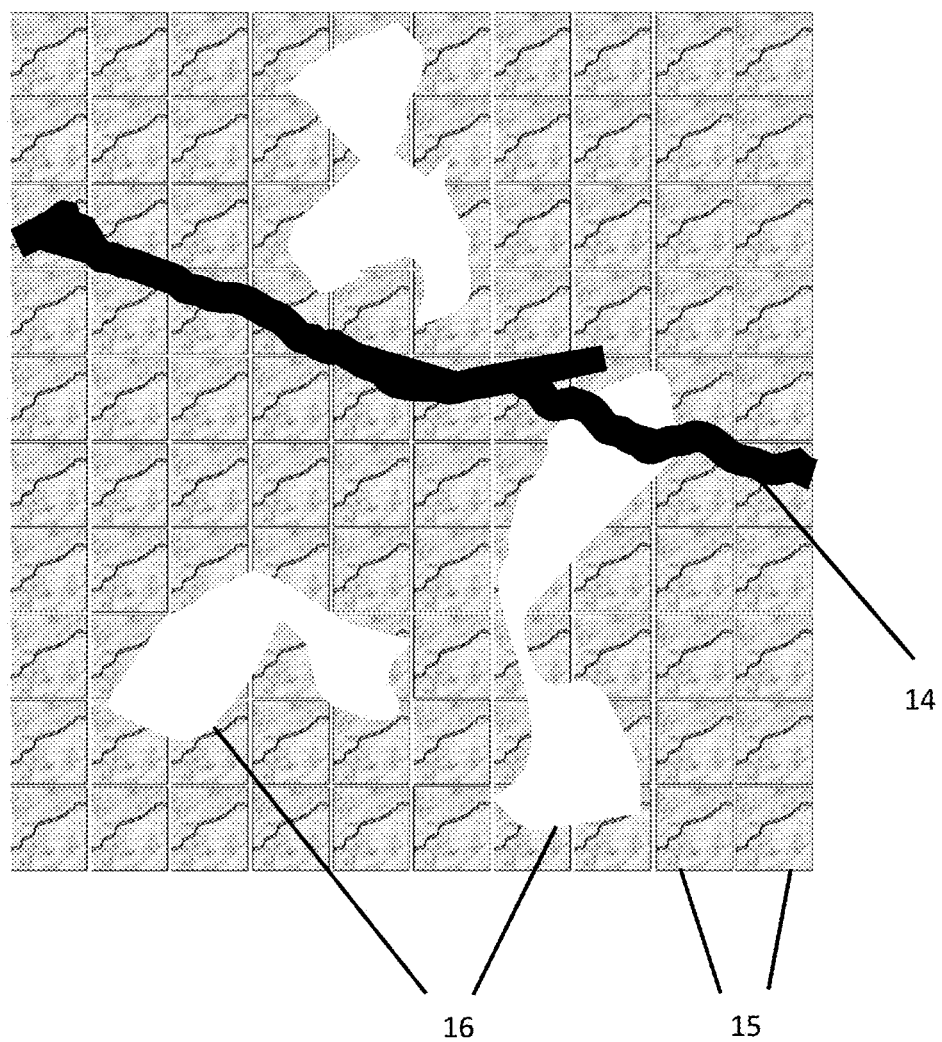
FIG. 5 illustrates images obtained by reconciling characteristic large-scale flow features into the binary images, according to aspects of the present embodiments.

FIG. 5 illustrates images obtained by reconciling characteristic large-scale flow features into the binary images at step 410, according to aspects of the present embodiments. In some embodiments, step 410 incorporates more or additional detailed data (for example, existence, sizes, lengths, and features of vugs 16, 18 (not shown), and/or fractures 14) that may not be captured at step 403 (that is, thin section images). The different pore features captured from the replicates 15 are connected by attaching the right pore throat together with those of similar features. This allows the systems of the present embodiments to capture the major pore types in a heterogeneous rock. As such, after classifying the pores and lumping them into the three major pore classes (for example, matrix 12, vugs 16, 18, and fractures 14,) each replicate 15 may be designed to be in relation to the overall network design. It is critical that the generated pore network as a result of connecting the replicates 15 together do not cause any fluid flow blockages. Any fluid that is injected via the injection ports, should flow continuously to allow fluid-fluid and fluid-pore interactions. Failure of the whole design may be caused by creating blockage and injectivity problems. Thus, replicated fractures (that is, replicates 15) should be carefully connected together to capture the required pore channel and vugs, in order to represent actual rock system.

Figure 6:
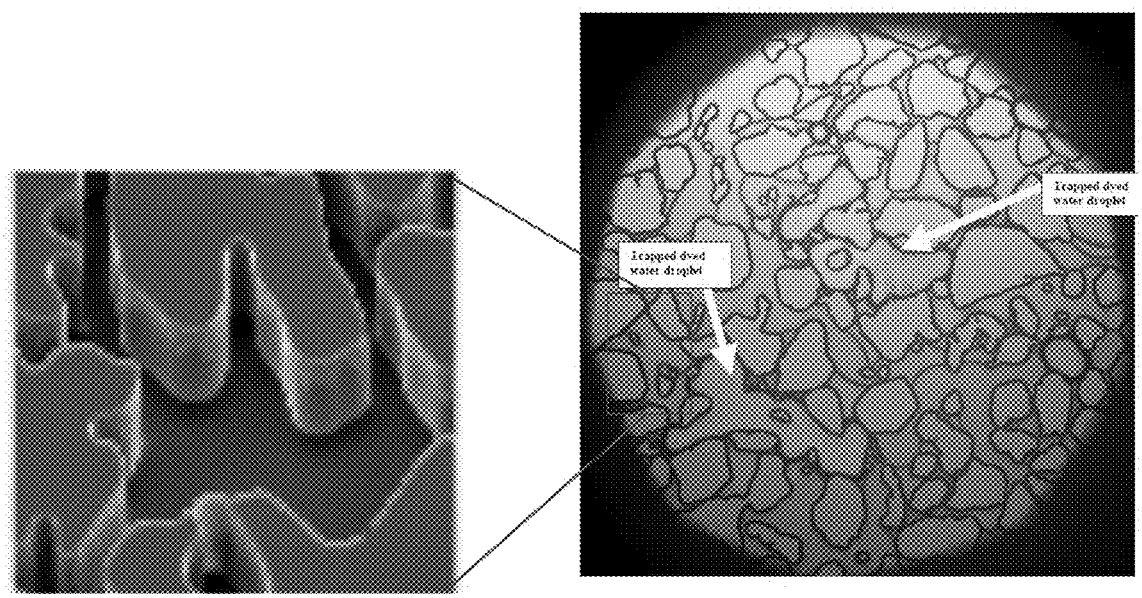
FIG. 6 illustrates images of generating layers, according to aspects of the present embodiments.

FIG. 6 illustrates images of generating and/or etching layers at step 412, according to aspects of the present embodiments. In some embodiments, step 412 may include using micro- and/or nano-fabrication (for example, lithography, film deposition, etching, boding, self-assembly, nanopatterning, X-ray) and/or electron microscopy (for example, SEM, TEM, et cetera) for fabricating (for example, etching, cleaning, characterizing, etc.) the micromodel. In some embodiments, step 412 may include using 3D printing machines to construct the micromodel according to a predetermined design.

Figure 7:
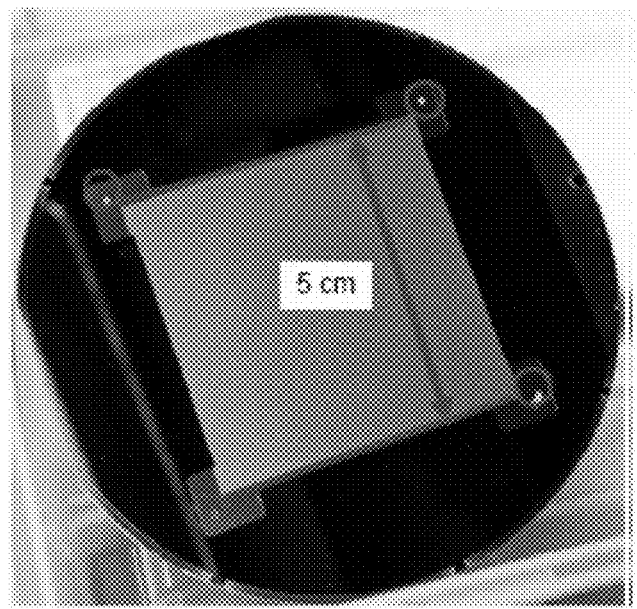
FIG. 7 illustrates an advanced micromodel, according to aspects of the present embodiments.

FIG. 7 illustrates the advanced micromodel, according to aspects of the present embodiments. In some embodiments, after completing the fabricating and etching of the model, the model is put inside a sealing ring. Step 414 may include compacting and/or assembling to seal off the whole system including the micromodel to ensure no leaking during injection of fluids. In some embodiments, the micromodel may be square, rectangular, circular, polygonal, or other suitable shapes. The micromodel may have a size from about 1 mm×1 mm×0.01 mm to about 1000 mm×1000 mm×1000 mm, from about 1 mm×1 mm×1 mm to about 100 mm×100 mm×100 mm, from about 10 mm×10 mm×10 mm to about 50 mm×50 mm×50 mm, from about 15 mm×15 mm×15 mm to about 50 mm×50 mm×50 mm, or from about 30 mm×30 mm×15 mm to about 40 mm×40 mm×40 mm. In some embodiments, the micromodel may have a preferred size. In some embodiments, the preferred size may depend on the size of a holder available in a lab. In some embodiments, the preferred size may depend on the microscope and the degree of movement that may be handled with relative accuracy to capture different sections, and to capture a similar position as the injection process. In some embodiments, the preferred size may depend on the pumps and relative accuracy in terms of volumetric rates. For example, highly accurate pumps may enable use of small sizes. In some embodiments, having microscopy that produces the depth of the micromodel may allow a study of more representative flow in a 3D system in terms of flow and structures. In some embodiments, the preferred size may depend on the dimension of flow features (for example, lengths of fractures and/or volumes of vugs) that may be inserted or captured.

Figure 8:
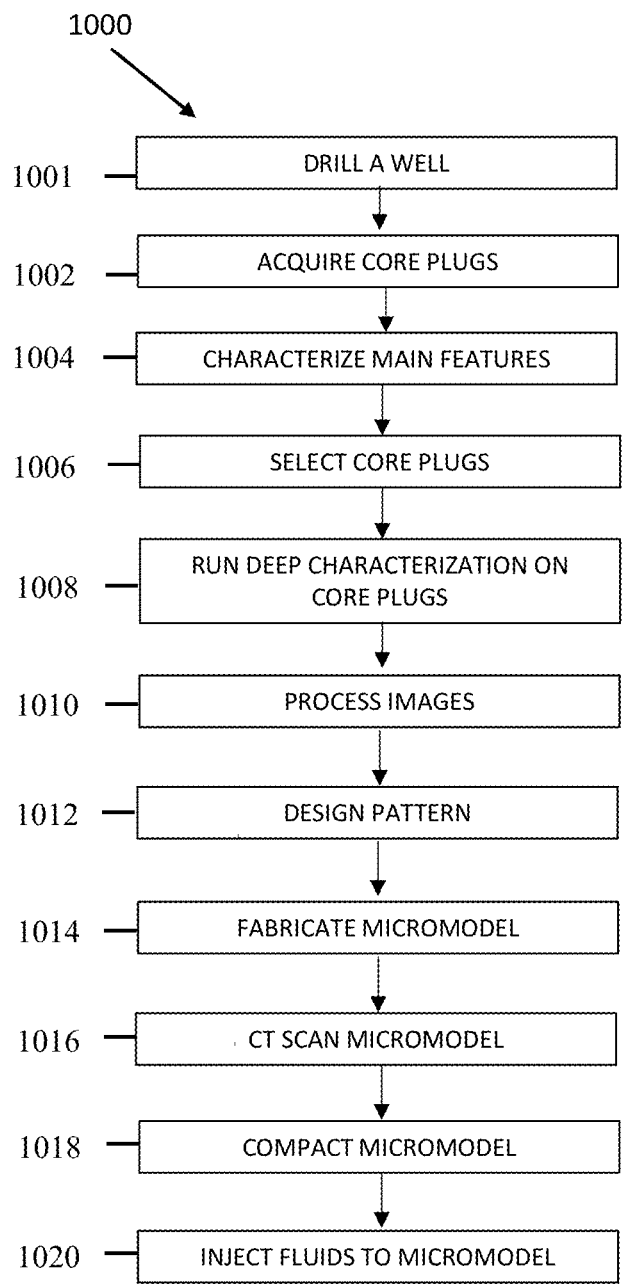
FIG. 8 illustrates a method for generating an advanced micromodel, according to aspects of the present embodiments.

FIG. 8 illustrates a method 1000 for fabricating an advanced micromodel, according to aspects of the present embodiments. At step 1001, method 1000 may include drilling a well. At step 1002, method 1000 may include coring in the well for acquiring core plugs from zones of interest in the well. At step 1004, method 1000 may include characterizing main features in the well using techniques such as logging, and/or PTA testing. In some embodiments, the logging may include gamma ray and sonic data (while drilling), in addition to FMI, to describe fractures along a wellbore. There may be two types of FMI: one may be conducted at the wellbore level and another may be conducted in the lab using cores, which may have a size range between about 12 feet to a few inches (for example, 1, 2, and/or 3 inches). Using the collected data from the techniques, fractures and main features of the well or well plugs may be identified and characterized. At step 1006, method 1000 may include screening the core plugs to select the best ones (for example, the ones that captures the most porosity features among the core plugs) for the design of a micromodel. At step 1008, method 1000 may include running deep lab imaging techniques (for example, FMI and/or CT scan) on the core plugs selected at step 1006. This may provide a deeper characterization with images that capture details such as size, length, and other features of fractures and/or vugs in the selected core plugs.

Referring still to FIG. 8, at step 1010, method 1000 may include processing (for example, quality controlling) images obtained from previous steps to ensure no blockage could occur before fabrication. In some embodiments, the method 1000 may include an image analysis on the cores and their thin sections to classify different pore systems and how they are connected to each other. In some embodiments, the produced images may be taken in 2D and/or 3D. In some embodiments, each image may be different from each other. For example, some images may have more features than others. Accordingly, images that contains all features of interest including fractures, matrix, and vugs may be used directly with minimal image processing, while images that contains only 1-2 of the desired features may require further processing to add missing features based on the information collected during step 1004.

Referring still to FIG. 8, at step 1012, method 1000 may include designing a pattern for a micromodel based on the image processed from step 1010. In some embodiments, step 1012 may include using a computer device and/or software. At step 1014, method 1000 may include sending a designed pattern (for example, via a computer device) to a physical surface after image processing from step 1010 for etching and fabrication of a final micromodel. In some embodiments, the etching may be done using commercial materials (for example, silicon wafers.) At step 1016, method 1000 may include generating a CT scan of the micromodel to ensure a well-connected pore system and accurate feature properties are produced between replicates 15, as designed. At step 1018, the method 1000 may include compacting (for example, assembling, sealing off, etc.) the micromodel to ensure no malfunction in next steps (for example, leakage during fluid injection, and/or uncharacteristic boundary effects.) For example, an envisioned end product may be a physical model that may accurately replicate all major features of an actual reservoir system. At step 1020, method 1000 may include injecting fluids into the micromodel for studying flow features or behaviors (for example, fluid movement) in a porosity system that the micromodel may represent. The method 1000 may include additional steps not shown in FIG. 8. In addition, in some embodiments of method 1000, not every step is performed. Method 1000 may also include performing steps in a different order than what is shown in FIG. 8. For example, in some embodiments, method 1000 may include performing step 1006 (selecting the core plugs) before step 1004 (characterizing the main features).

Elements of different implementations described may be combined to form other implementations not specifically set forth previously. Elements may be left out of the processes described without adversely affecting their operation or the operation of the system in general. Furthermore, various separate elements may be combined into one or more individual elements to perform the functions described in this specification.

Other implementations not specifically described in this specification are also within the scope of the following claims.

These and other features, aspects, and advantages of the present invention will become better understood with reference to the following description and appended claims. The accompanying drawings, which are incorporated in and constitute a part of this specification, illustrate embodiments of the present disclosure and, together with the description, serve to explain the principles of the present embodiments.

Certain Definitions

In order for the present disclosure to be more readily understood, certain terms are first defined below. Additional definitions for the following terms and other terms are set forth throughout the specification.

As used herein, the term "reservoir" is used to describe a subsurface body of rock. In some embodiments, a reservoir may include porosity and permeability to store and/or transmit fluids.

As used herein, the term "well" is used to describe a hole drilled in the subsurface to reach a reservoir.

As used herein, the term "substantially" refers to the qualitative condition of exhibiting total or near-total extent or degree of a characteristic or property of interest.

As used herein, "a" or "an" with reference to a claim feature means "one or more," or "at least one."

EQUIVALENTS

It is to be understood that while the disclosure has been described in conjunction with the detailed description thereof, the foregoing description is intended to illustrate and not limit the scope of the invention(s). Other aspects, advantages, and modifications are within the scope of the claims.

This written description uses examples to disclose the invention, including the best mode, and also to enable any person skilled in the art to practice the present embodiments, including making and using any devices or systems and performing any incorporated methods. The patentable scope of the present embodiments is defined by the claims, and may include other examples that occur to those skilled in the art.

What is claimed is:

1. A process of constructing a micromodel for a multiple porosity system comprising:
   drilling a well;
   coring the well to acquire core plugs from the well;
   producing thin section images of the core plugs for acquiring a first feature of the core plugs;
   transforming the thin section images to binary images;
   characterizing flow features using one or more fracture characterization techniques for acquiring a second feature of the core plugs;
   reconciling the first and second features into the binary images for designing a pattern for the micromodel;
   fabricating the micromodel based on the pattern using a computer device,
   where reconciling the first and second features into the binary images further comprises connecting replicates by attaching appropriate pore throats of the same features together.

2. The process of claim 1, further comprising:
   replicating the binary images for expanding a computer network for modeling the well.

3. The process of claim 1, further comprising compacting the micromodel.

4. The process of claim 1, where the one or more characterization techniques comprise at least one of formation micro-imager (FMI) logging, pressure transient analysis (PTA), and CT scan.

5. The process of claim 1, where the multiple porosity system is a triple porosity system.

6. The process of claim 1, where the second feature comprises features of vugs and micro-fractures.

7. The process of claim 1, where the flow features comprise large vugs and macro fractures.

8. The process of claim 1, where the flow features come from sources comprising one or more of well logs, pressure transient tests, whole cores visual descriptions, and images.

9. The process of claim 1, where the vugs comprise a dimeter from about 0.1 mm to 50 mm.

10. The process of claim 3, further comprising capturing attributes of the multiple porosity system, the attributes comprising at least one of types, distributions, wettability, tortuosity, and dimensions of pores, cracks, pore throats, fractures, and vugs.

11. A method for generating a micromodel comprising:
drilling a well;
coring in the well for acquiring core plugs from zones in the well;
characterizing main features in the well;
screening the core plugs to select the ones that capture the most porosity features;
running deep lab imaging techniques on the selected core plugs for capturing details in the selected core plugs;
reconciling the details into images for designing a pattern for the micromodel, where reconciling the details into the images comprises connecting replicates by attaching appropriate pore throats of the same details together;
processing the images obtained from previous steps;
designing the pattern based on processed images; and
sending the pattern to a physical surface for fabricating the micromodel.

12. The method of claim 11, where characterizing main features in the well comprises using at least one of logging and pressure transient analysis (PTA) testing.

13. The method of claim 12, where using at least one of logging and pressure transient analysis (PTA) testing comprises generating at least one of gamma ray and sonic data while drilling to describe fractures along a wellbore.

14. The method of claim 11, where deep lab imaging techniques comprise formation micro-imager (FMI), where the FMI is conducted in the well.

15. The method of claim 11, where deep lab imaging techniques comprise formation micro-imager (FMI), where the FMI is conducted over cores in a lab.

16. The method of claim 11, where deep lab imaging techniques comprise a CT scan.

17. The method of claim 11, where the details comprise at least a size and length of fractures and vugs.

18. The method of claim 11, where images are taken in at least one of 2D and 3D.

19. The method of claim 11, further comprising:
compacting the micromodel; and
injecting fluids into the micromodel.

20. The method of claim 11, where the one or more characterization techniques comprise formation micro-imager (FMI) logging, pressure transient analysis (PTA), and a CT scan.

21. The method of claim 12, where using at least one of logging and PTA testing comprises generating gamma ray and sonic data while drilling to describe fractures along a wellbore.

* * * * *